United States Patent
Taylor et al.

(10) Patent No.: US 9,402,622 B2
(45) Date of Patent: Aug. 2, 2016

(54) EXTERNAL SUTURE SECUREMENT DEVICES AND METHODS

(71) Applicant: Cook Medical Technologies LLC, Bloomington, IN (US)

(72) Inventors: James A. Taylor, Bloomington, IN (US); Gary L. Neff, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 108 days.

(21) Appl. No.: 14/155,988

(22) Filed: Jan. 15, 2014

(65) Prior Publication Data

US 2014/0222073 A1 Aug. 7, 2014

Related U.S. Application Data

(60) Provisional application No. 61/752,683, filed on Jan. 15, 2013.

(51) Int. Cl.
*A61B 17/04* (2006.01)
*A61B 17/02* (2006.01)

(52) U.S. Cl.
CPC ......... *A61B 17/0487* (2013.01); *A61B 17/0218* (2013.01); *A61B 2017/0417* (2013.01); *A61B 2017/0419* (2013.01); *A61B 2017/0464* (2013.01); *A61B 2017/0496* (2013.01)

(58) Field of Classification Search
CPC ........... A61B 17/0401; A61B 17/0487; A61B 17/046; A61B 2017/0409; A61B 2017/0412; A61B 2017/0414; A61B 2017/0464; A61B 2017/042; A61B 2017/0422; A61B 2017/0424; A61B 2017/0425; A61B 2017/043; A61B 2017/0432; A61B 2017/0433; A61B 2017/0446; A61B 2017/045; A61B 2017/0454; A61B 2017/0462; A61B 2017/0488
USPC ........................................................ 606/232
See application file for complete search history.

(56) References Cited

U.S. PATENT DOCUMENTS

| | | | |
|---|---|---|---|
| 5,258,015 A * | 11/1993 | Li et al. | 606/232 |
| 5,383,905 A | 1/1995 | Golds et al. | |
| 5,681,351 A | 10/1997 | Jamiolkowski et al. | |
| 7,090,690 B2 | 8/2006 | Foerster et al. | |
| 8,057,511 B2 * | 11/2011 | Flores et al. | 606/232 |
| 2001/0018597 A1 * | 8/2001 | Gellman | A61B 17/00234 606/198 |
| 2012/0065648 A1 * | 3/2012 | Roorda | A61B 17/0487 606/148 |

OTHER PUBLICATIONS

Dow-Corning Elastomer Definition.*

* cited by examiner

*Primary Examiner* — Jonathan Miles
*Assistant Examiner* — Kankindi Rwego
(74) *Attorney, Agent, or Firm* — Woodard, Emhardt, Moriarty, McNett & Henry LLP

(57) ABSTRACT

Described are devices, methods and systems for securing sutures external to the body. In certain aspects, a suture securement device includes a housing member defining an internal cavity and a wedge member moveable within the cavity between a suture-release position to a suture-retention position. The wedge member defines a suture aperture extending therethrough. At the suture-retention position, the housing member is configured to compress the wedge member to clamp the suture, thereby substantially preventing the suture from moving within the aperture.

23 Claims, 3 Drawing Sheets

EXTERNAL SUTURE SECUREMENT DEVICES AND METHODS

BACKGROUND

The present disclosure relates generally to medical technology and in particular aspects to devices, methods and systems for securing sutures external to the patient's body. As further background, there exist a variety of medical procedures in which suture and anchor sets are necessary to secure patient tissue before, during and/or after the procedure. In such procedures, it is often necessary to secure the suture material outside of the body to ensure that the corresponding anchor device maintains its position. Many aspects of such procedures often rely, in part, on the successful securement of the suture material outside of the body.

Several methods have been suggested for securing suture material, including various methods of tying the suture or crimping the suture. However, such arrangements can lose integrity over time or upon the application of force along the suture and anchor set. Additionally, such arrangements can be difficult to implement and/or uncomfortable to the patient.

There remain needs for improved and/or alternative systems and methods for securing suture material external to the patient's body. The present disclosure is addressed to those needs.

SUMMARY

The present disclosure provides, in certain aspects, unique methods and systems for securing sutures external to the patient's body for use in medical procedures. In certain embodiments, the present disclosure provides unique methods and systems for securing sutures via clamping sutures through compressive forces.

In one embodiment, a suture securement system includes a housing member defining an internal cavity and a wedge member moveable within the cavity. The wedge member includes a suture aperture through which a suture is threaded. Movement of the wedge member into a compression portion of the cavity causes the wedge member to clamp the suture to secure it.

In another embodiment, a suture securement system includes a housing member defining an internal cavity with a larger end and a smaller end, and a wedge member moveable within the cavity. The wedge member includes a suture aperture through which a suture is threaded. When the wedge member is moved toward the smaller end of the cavity, the housing member compresses the wedge member such that the diameter of the suture aperture is reduce thereby imparting a clamping force on the suture.

In yet another embodiment, a suture securement system includes a housing member defining an internal cavity and a wedge member moveable within the cavity between a suture-release position and a suture-retention position. The wedge member includes a suture aperture through which a suture is threaded. When the wedge member is positioned within the cavity at the suture-retention position, the wedge member is compressed such that the wedge member clamps the suture to secure it.

Other objects, embodiments, forms, features, advantages, aspects, and benefits of the present disclosure shall become apparent from the detailed description and drawings included herein.

DETAILED DESCRIPTION

Figure 1:
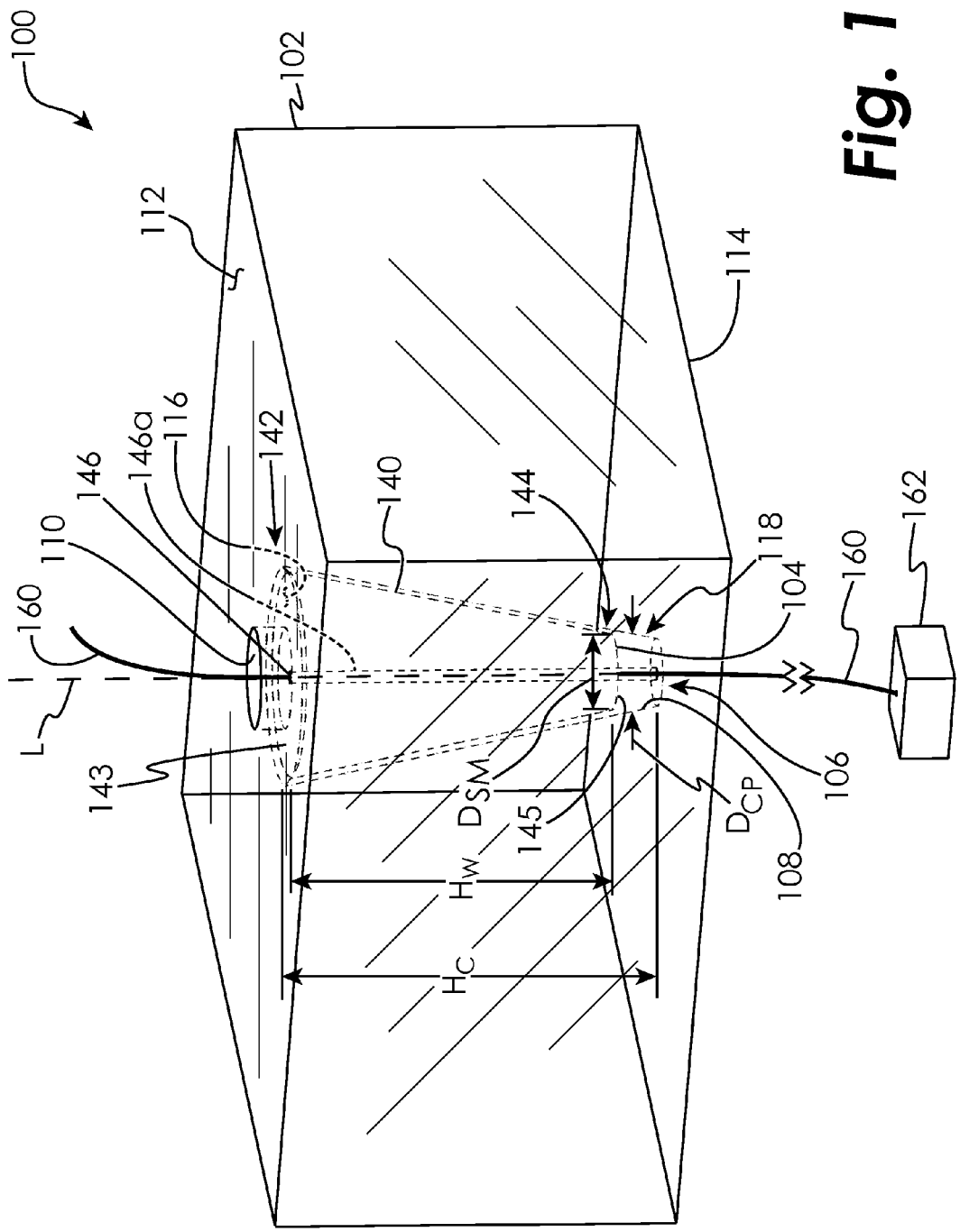
FIG. 1 is a perspective view of an inventive medical system according to an embodiment of the present disclosure.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Figure 2:
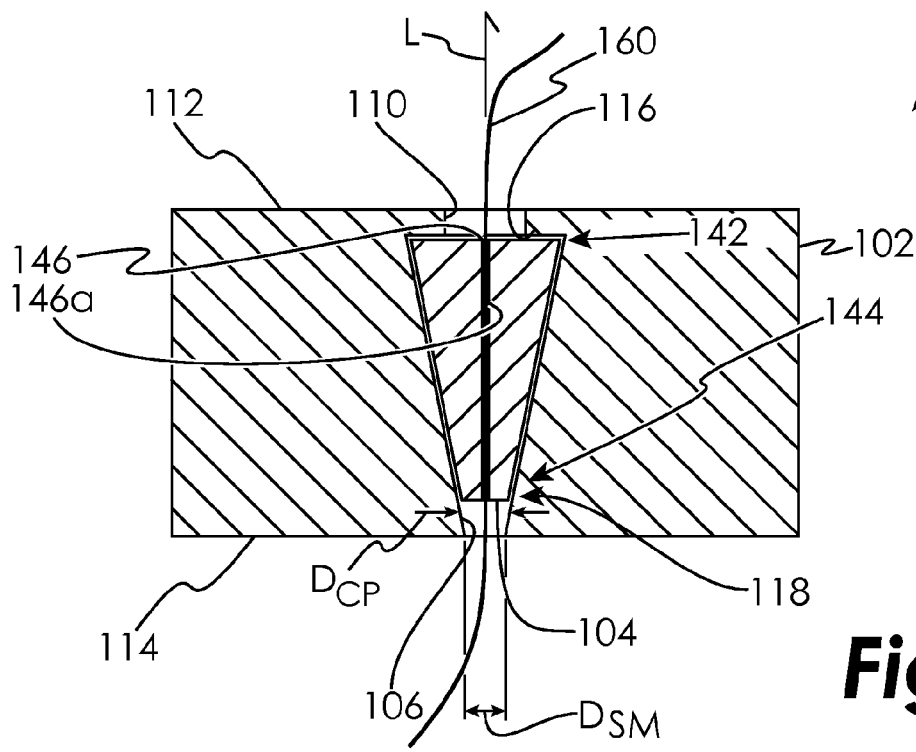
FIG. 2 is a side cross-sectional view of the medical system of FIG. 1.
Figure 3:
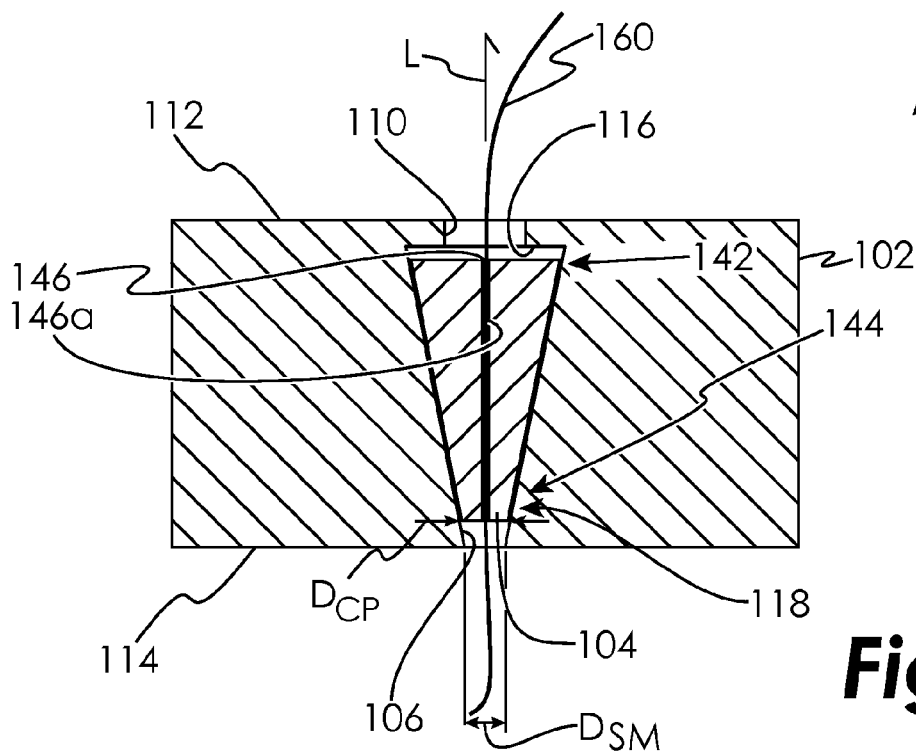
FIG. 3 is another side cross-sectional view of the medical system of FIG. 1.
Figure 4:
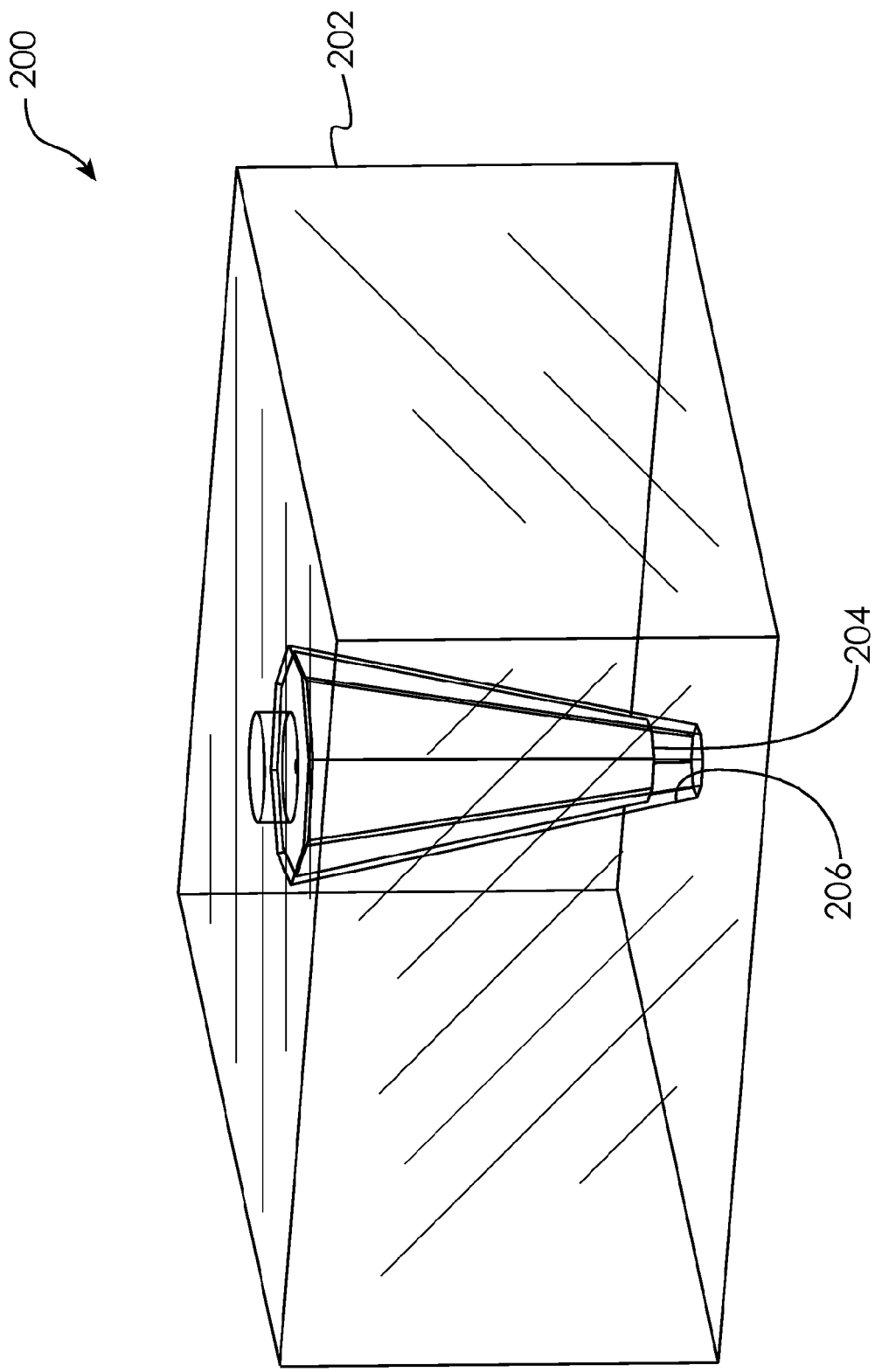
FIG. 4 is a perspective view of an inventive medical system according to another embodiment of the present disclosure.

In certain aspects, the present disclosure provides unique methods and systems for securing sutures external to the patient's body in a variety of medical procedures. Many medical procedures utilize sutures to engage with and apply tension to anchors or other devices which are positioned within the patient's body. To apply and maintain the appropriate tension force on the anchor, it is necessary to secure the suture material outside of the body. The present disclosure provides for a suture securement system which clamps the suture material to frictionally secure it. The system includes a housing member defining an internal cavity and a tapered wedge moveable within the cavity. The wedge defines an aperture through which a suture may be threaded. Relative movement of the wedge within the cavity causes the housing member to impart a compressive force on the wedge member thereby imparting a clamping force on the suture to substantially prevent movement of the suture. FIGS. 1 through 3 illustrate one non-limiting example of a suture securement system according to one embodiment of the present disclosure. FIG. 4 illustrates another non-limiting example of a suture securement system according to another embodiment of the present disclosure.

With reference now to FIGS. 1 through 3, there is shown a suture securement system 100 according to one embodiment of the present disclosure. In this illustrative arrangement, a housing member 102 and a wedge member 104 cooperate to frictionally clamp a suture within the wedge member 104. The illustrated housing member 102 defines an internal cavity 106 extending along a longitudinal axis L. Optionally, the housing member 102 may also define an internal access passage 110 in communication with the cavity 106. The illustrated cavity 106 is substantially conical in shape and is defined by an internal truncated conical surface 108 and an upper limit surface 116. Additionally, the housing member 102 may have a top exterior surface 112 and a bottom exterior surface 114. For purposes of illustration, the housing members 102 and 202 are shown as transparent in FIGS. 1 and 4 for ease of illustration of the wedge members 104 and 204.

The illustrated wedge member 104 is substantially conical in shape and includes an external truncated conical surface 140 extending between a top surface 143 and a bottom surface 145. The illustrated wedge member 104 tapers from a larger end 142 (generally at top surface 143) to a smaller end 144 (generally at bottom surface 145). The wedge member 104 defines a suture aperture 146 defined by a wall surface 146a and being configured to receive an example suture 160. In the illustrated embodiment, suture aperture 146 extends between top and bottom surfaces 143 and 145 substantially along longitudinal axis L. However, it should be appreciated that the suture aperture may be arranged differently within the wedge member as would occur to one of ordinary skill in the art. In certain embodiments, the wedge member 104 is a solid and continuous mass about aperture 146, such that aperture wall 146a is an unbroken, continuous surface about the aperture 146.

The wedge member 104 is moveable within cavity 106 along the longitudinal axis L between a suture-release position (as shown in FIG. 2) and a suture-retention position (as shown in FIG. 3). In certain embodiments, the height $H_C$ of cavity 106 is larger than the height $H_W$ of wedge member 104 such that the wedge member 104 is moveable or slideable within the cavity 106. At the suture-release position in FIG. 2, the suture 160 is freely moveable within suture aperture 146.

At the suture-retention position in FIG. 3, the suture 160 is clamped by the wedge member 104 such that the suture 160 is substantially prevented from moving within the aperture 146. More specifically, the housing member 102 and 104 are sized and configured such that, at the suture-retention position, the housing member 102 imparts a compressive force on the wedge member 104 which thereby squeezes or clamps the suture 160 within aperture 146. In this way, the aperture wall surface 146a is compressed against the suture 160 to contact the suture 160 in a gripping fashion to substantially prevent movement. To accomplish this, member 104 is "wedged" into the smaller end of the cavity 106. In the illustrated embodiment, cavity 106 includes a compression portion 118 at the smaller end of the cavity adjacent exterior bottom surface 114. The cavity 106 defines a series of diameters $D_{CP}$ at the compression portion 118. The smaller end 144 of wedge member 104 defines a diameter $D_{SM}$. In certain embodiments, the diameter $D_{SM}$ is larger than the diameters $D_{CP}$ such that as the smaller end 144 enters the compression portion 118, the wedge member 104 is compressed by the housing member 102 thereby clamping the suture 160.

It is also contemplated that, in other embodiments, the system 100 may include a supplemental locking mechanism for securing the wedge member at the suture-retention position, in addition to the frictional wedge or compression forces. The supplemental locking mechanism may be any of a variety of suitable locking mechanisms as would occur to one of ordinary skill in the art. In certain optional embodiments, the wedge member 104 and housing member 102 may be fastened together in a suitable manner, such that the wedge member 102 remains moveable within cavity 106 while substantially preventing unwanted separation of the components.

It should be appreciated that the particular elements and features of housing member 102 and wedge member 104 may be configured differently as would occur to one of ordinary skill in the art. For example, it should be appreciated that the suture aperture 146 may be positioned and orientated differently, such as angled and oblique to the longitudinal axis L. Additionally, it should be appreciated that the illustrated arrangement is one non-limiting example of the possible manners of sliding, wedging and/or clamping engagement between the wedge member 104 and the housing member 102.

Additionally, it is contemplated that the housing member 102 and wedge member 104, separately and/or collectively, may be shaped, sized and/or configured differently as would occur to one of ordinary skill in the art. In the illustrated embodiment, the housing member 102 is generally shaped as a cube, although it is contemplated that the housing member 102 could assume a different overall shape as would occur to one of ordinary skill in the art. In one example embodiment, the housing member assumes overall dimensions of about half (½) of an inch in length and width as a square cross-section and one quarter (¼) of an inch in height. However, other suitable and appropriate sizes of the system components are contemplated. Additionally, the illustrated access passage 110 is cylindrical in shape, but could also be shaped differently.

In the illustrated embodiment, the cavity 106 and wedge member 104 are shaped as conical frustums with circular cross-sections; however, it should be appreciated that these elements may also be shaped differently, such as having non-circular cross-sectional shapes including oval, square, triangular, rectangular, hexagon, octagon, and so on. In other shaped systems, preferably the dimension of the wedge member at its smaller end is generally larger than the dimension of the cavity at the compression portion to provide the necessary compressive force to clamp the suture.

As one example, FIG. 4 shows a differently-shaped suture securement system for illustration purposes. System 200 illustrated in FIG. 4 includes a wedge member 204 and a housing member 202 defining a cavity 206. As shown, the illustrated wedge member 204 and cavity 206 are octagonal in cross-sectional shape. The system 200 provides suture securement in substantially the same manner as system 100, including movement between a suture-release position at a larger end and a suture-retention position at a smaller end. Although systems 100 and 200 illustrate internal cavities and wedge members of corresponding or matching cross-sectional shapes, it is contemplated that non-matching shapes of these components may also be used.

With reference to FIGS. 1-3, an example method of securing a suture will be discussed with respect to an example medical procedure requiring the use of a suture and anchor combination. In the illustrated example procedure, a suture 160 is engaged with an optional anchor 162 in an appropriate manner which is not critical to the present disclosure (see FIG. 1). An introducer needle or other suitable delivery instrument may be used to introduce, deploy and/or secure the suture 160 and anchor 162 combination in the patient's body. The suture and anchor set may be utilized in a variety of medical applications to secure tissue in the body. As one example, one or more suture and anchor sets may be used to secure the patient's stomach to the abdominal or peritoneal wall to allow for insertion and placement of a catheter or other medical device into the patient's stomach. However, it should be appreciated that suture and anchor sets are utilized in a variety of other medical applications. Additionally, it should be appreciated that the suture to be secured may be engaged with a different internally disposed device, or in some applications, the internal device is absent and the suture is directly secured to tissue inside the patient's body.

As part of a typical medical procedure, the suture extends from the anchor or similar device through the patient's body to a point external to the body. The suture is pulled in tension which thereby pulls the anchor firmly against the patient's tissue to be secured. To maintain the tension along the suture, the suture is secured external to the patient's body, for example utilizing system 100.

Prior to use of system 100, wedge member 104 is pre-positioned in cavity 106 within housing member 102. A portion of the suture 160 is threaded through suture aperture 146. Upon threading, the suture is readily moveable through the aperture while wedge member 104 is positioned at the suture-release position (see FIG. 2). In some embodiments, the housing member 102, the wedge member 104, the suture 160 and/or the optional anchor 162 may be delivered to a medical professional in a pre-loaded and/or pre-engaged manner prior to use of the system 100, such as the pre-loaded arrangement shown in FIG. 1. After the suture is suitably threaded and the suture and anchor set is positioned within the patient's body as desired, the medical professional using system 100 may adjust the position of the housing member 102 (with wedge member 104 positioned therein) such that the bottom exterior surface 114 is positioned against the patient's skin. It is contemplated that, in certain embodiments, suitable material pieces may optionally be placed between the housing member and the patient's skin to protect the skin and/or provide comfort to the patient.

After the suture 160 is threaded through aperture 146 and pulled in a significant amount of tension, e.g. with housing member 102 against or supported by the patient's skin as noted, wedge member 104 is moved downward along longitudinal axis L into compression portion 118 to a suture-retention position (see FIG. 3). The movement occurs in a direction from upper limit surface 116 toward bottom exterior surface 114. In the illustrated embodiment, the medical professional gains access to the wedge member 104 through access passage 110. In certain embodiments, a medical professional may simultaneously push the wedge member 104 toward compression portion 118 while also holding the suture 160 in tension. As the smaller end 144 of wedge member 104 enters diametrically-smaller compression portion 118, the housing member 102 exerts a compression force on the wedge member 104 which thereby clamps the suture 160 to secure it. In other words, the housing member 102 causes the wedge member 104 to inwardly compress to reduce the diameter of suture aperture 146 and thereby frictionally retain the suture 160 therein. The clamping of suture 160 prevents or limits suture 160 from moving through the suture aperture 146 and thereby maintains tension along the suture and the associated anchoring device, as necessary to the particular medical procedure being performed.

In certain embodiments, the frictional interference fit between wedge member 104 and housing member 102 may be sufficient to maintain the positioning of wedge member 104 at the suture-retention position. In other embodiments, as mentioned above, an optional locking mechanism may be used, as would occur to one of ordinary skill in the art, to further secure the position of the wedge member 104 within housing member 102 at the suture-retention position.

In certain embodiments, accessing, manipulating and/or removing the suture and/or the anchor to which the suture is engaged requires cutting the suture at a location between the patient's skin and housing member 102. In alternative embodiments, wedge member 104 may be moved back to the suture-release position (as shown in FIG. 2) to allow for access to or manipulation of the suture. Following the necessary access or manipulation, the wedge member 104 may be moved down again along longitudinal axis L to clamp the suture and secure its position.

In certain embodiments, the systems discussed herein may be utilized in multiple to secure multiple sutures to allow for the insertion and placement of a catheter or other medical device. In such embodiments, the catheter is inserted centrally between the multiple systems and sutures within a catheter placement zone. In a particular example embodiment, three system and sutures are arranged in a triangular pattern, with the catheter being inserted centrally between the triangular arrangement of suture securement systems.

The components of the systems disclosed herein may be formed with a variety of biocompatible polymer materials. As examples, the housing members and wedge members may be composed of suitable polymer materials. In one particular example embodiment, the housing members are formed of sufficiently rigid polymer materials and the wedge members are composed of sufficiently compressible and/or elastomeric polymer materials. Regarding suture 160, while suture material in particular will be useful in certain embodiments, a variety of other elongate materials and objects capable of being anchored can be used as an alternative to, or in addition, to suture material. These include various types of cords, filaments, chains, strings, wires and other similar objects having relatively slender profiles for extending through patient tissue.

Any or all of the components described herein can be provided in a sterile pack for providing necessary parts, or a variety of parts, to a surgeon. For example, one or more predetermined types or sizes of introducer needle, engaged suture and anchor combination, and suture securement system may be provided in a single sterile package or kit. A surgeon can choose the sizes or types of components he or she wishes to use during surgery. Alternatively, sterile kits containing predetermined sizes or types of components may be provided. Packages or kits of the components described herein can include additional devices or tools which may be useful in the particular medical procedure being performed.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

What is claimed is:

1. An external suture securement apparatus, comprising:
   a housing member defining an internal cavity extending along a longitudinal axis, the cavity having a larger end and a smaller end; and
   a wedge member positioned and moveable within the cavity along the longitudinal axis, wherein the wedge member defines a suture aperture extending therethrough and being adapted to receive a suture and wherein the wedge member has an external upper surface, an external lower surface and an external side surface, the suture aperture having respective openings through the upper and lower surfaces and the side surface being unbroken and continuous around the entirety of the suture aperture;
   wherein, when the wedge member is moved toward the smaller end of the cavity, the wedge member is compressed by the housing member such that the diameter of the suture aperture is reduced thereby imparting a clamping force on the suture to substantially prevent the suture from moving with the aperture, and
   wherein the wedge member is configured to move within the cavity from a suture-release configuration in which the suture is freely moveable within the aperture to a suture-retaining configuration and wherein the entirety of the wedge member is located in the internal cavity when the wedge member is located in either the suture-release configuration or the suture-retaining configuration.

2. The apparatus of claim 1, wherein at the suture-retaining configuration, the wedge member is positioned at or near the smaller end of the cavity, and at the suture-release configuration, the wedge member is positioned at or near the larger end of the cavity such that the suture is freely moveable within the aperture.

3. The apparatus of claim 1, wherein the internal cavity and the wedge member are shaped as conical frustums.

4. The apparatus of claim 1, wherein the cavity includes a compression portion adjacent the smaller end of the cavity, wherein the wedge member includes a smaller end having a diameter, wherein the compression portion defines diameters which are smaller than the diameter of the smaller end of the wedge member, whereby when the smaller end of the wedge member enters the compression portion, the housing member is configured to impart a compressive force on the wedge member to clamp the suture.

5. The apparatus of claim 1, wherein the housing member includes opposing top and bottom exterior surfaces and defines an access passage extending from the top exterior surface to the larger end of the cavity, wherein the access passage is in communication with cavity.

6. The apparatus of claim 1, further comprising a suture extending through the suture aperture of the wedge member and a suture anchor engaged with the suture.

7. The apparatus of claim 1, wherein the housing member is composed of a substantially rigid polymer material and the wedge member is composed of a sufficiently compressible polymer material.

8. The apparatus of claim 1, wherein the wedge member has a maximum diameter measured perpendicular to the suture aperture, and wherein the housing member has first and second opposed surfaces with the larger end of the cavity nearer to the first surface than to the second surface and the smaller end of the cavity nearer to the second surface than to the first surface, and wherein the first surface opens to an access passage that communicates with the larger end of the cavity, the access passage being smaller than the larger end of the cavity and smaller than the maximum diameter of the wedge member.

9. An external suture securement apparatus, comprising:
a substantially rigid housing member defining a cavity;
an elastomeric wedge member positioned and moveable within the cavity, wherein the wedge member defines a suture aperture extending therethrough and being adapted to receive a suture; and
a suture extending through the suture aperture;
wherein the wedge member is moveable within the cavity from a suture-release position to a suture-retention position, wherein at the suture-release position, the suture is freely moveable within the aperture, wherein at the suture-retention position, the wedge member is compressed by the housing member such that the wedge member clamps the suture to substantially prevent the suture from moving within the aperture and the wedge member is held by the housing member entirely within the cavity, and
wherein the entirety of the wedge member is located in the cavity when the wedge member is located in either the suture-release configuration or the suture-retaining configuration.

10. The apparatus of claim 9, wherein the internal cavity and the wedge member are shaped as conical frustums.

11. The apparatus of claim 9, wherein the cavity includes a compression portion defining a series of diameters, wherein the wedge member includes a smaller end having a diameter, wherein the diameters of the compression portion are smaller than the diameter of the smaller end of the wedge member, whereby when the smaller end of the wedge member enters the compression portion, the housing member is configured to impart a compressive force on the wedge member to clamp the suture.

12. The apparatus of claim 9, wherein the housing member includes opposing top and bottom exterior surfaces and defines an access passage extending from the top exterior surface to the larger end of the cavity, wherein the access passage is in communication with cavity.

13. The apparatus of claim 9, further comprising a suture anchor engaged with the suture.

14. An external suture securement apparatus, comprising:
a housing member having an internal truncated conical cavity at least partially defined by an internal truncated conical surface, wherein the cavity extends from a larger end to a smaller end along a longitudinal axis; and
a tapered wedge member positioned and moveable within the cavity along the longitudinal axis, wherein the wedge member includes an external truncated conical surface extending between a larger end and a smaller end of the wedge member, wherein the wedge member defines a suture aperture extending therethrough and being adapted to receive a suture, the wedge member having an external upper surface, an external lower surface and an external side surface, the suture aperture having respective openings through the upper and lower surfaces and the side surface being unbroken and continuous around the entirety of the suture aperture;
wherein the cavity defines decreasing diameters from the larger end to the smaller end and includes a compression portion adjacent the smaller end of the cavity, wherein the compression portion defines diameters which are smaller than the diameter of the smaller end of the wedge member, whereby when the smaller end of the wedge member enters the compression portion, the housing member is configured to inwardly compress the wedge member to reduce the diameter of the suture aperture such that the suture is frictionally retained within the wedge member and substantially prevented from moving with the aperture, and
wherein the wedge member is configured to move within the cavity from a suture-release configuration in which the suture is freely moveable within the aperture to a suture-retaining configuration and wherein the entirety of the wedge member is located in the internal cavity when the wedge member is located in either the suture-release configuration or the suture-retaining configuration.

15. The apparatus of claim 14, wherein the cavity includes a height along the longitudinal axis from the larger end to the smaller end of the cavity and the wedge member includes a height along the longitudinal axis from the larger end to the smaller end of the wedge member, wherein the height of the cavity is larger than the height of the wedge member such that the wedge member is configured to be moveable within the cavity along the longitudinal axis.

16. The apparatus of claim 14, wherein the housing member includes opposing top and bottom exterior surfaces and defines an access passage extending from the top exterior surface to the larger end of the cavity, wherein the access passage is in communication with cavity.

17. The apparatus of claim 16, wherein the housing member includes an interior upper limit surface partially defining the cavity, with the cavity extending between the interior upper limit surface at the larger end of the cavity and the exterior bottom surface at the smaller end of the cavity.

18. The apparatus of claim 16, wherein the access passage is cylindrical in shape.

19. The apparatus of claim 14, wherein the cavity is in the shape of a conical frustum.

20. The apparatus of claim 14, wherein the suture aperture extends substantially along the longitudinal axis between the larger and smaller ends of the wedge member.

21. The apparatus of claim 14, further comprising a suture extending through the suture aperture of the wedge member and a suture anchor engaged with the suture.

22. The apparatus of claim 14, wherein the housing member is composed of a substantially rigid polymer material and the wedge member is composed of a sufficiently compressible polymer material.

23. The apparatus of claim 14, wherein when the wedge member is not positioned in the compression portion, the suture is freely moveable within the suture aperture.

* * * * *